United States Patent [19]

Mechley

[11] Patent Number: 5,399,088
[45] Date of Patent: Mar. 21, 1995

[54] ORTHODONTIC WIRE AND METHOD FOR THE MOVING OF TEETH

[76] Inventor: Michael E. Mechley, 9840 Winnebago Trail, Cincinnati, Ohio 45241

[21] Appl. No.: 176,709

[22] Filed: Jan. 3, 1994

[51] Int. Cl.⁶ .............................................. A61C 3/00
[52] U.S. Cl. .......................................... 433/20; 433/24
[58] Field of Search ........................ 433/18, 20, 21, 24

[56] References Cited

U.S. PATENT DOCUMENTS

| | | |
|---|---|---|
| 3,504,438 | 4/1970 | Wittman et al. |
| 4,037,324 | 7/1977 | Andreasen. |
| 4,197,643 | 4/1980 | Burstone et al. .................... 433/20 |
| 4,472,035 | 9/1984 | Takamura et al. ................... 351/41 |
| 4,490,112 | 12/1984 | Tanaka et al. ....................... 433/20 |
| 4,585,414 | 4/1986 | Kottemann .......................... 433/20 |
| 4,659,310 | 4/1987 | Kottemann .......................... 433/20 |
| 4,717,341 | 1/1988 | Goldberg et al. ..................... 433/9 |
| 4,849,032 | 7/1989 | Kawaguchi .......................... 433/21 |
| 5,017,133 | 5/1991 | Miura .................................. 433/20 |
| 5,018,969 | 5/1991 | Andreiko et al. ..................... 433/20 |
| 5,044,947 | 9/1991 | Sachdeva et al. ..................... 433/20 |
| 5,046,948 | 9/1991 | Miura .................................. 433/21 |
| 5,080,584 | 1/1992 | Karabin ............................... 433/20 |
| 5,092,941 | 3/1992 | Miura ............................. 148/11.5 N |
| 5,102,333 | 4/1992 | Suzuki et al. ........................ 433/24 |
| 5,131,843 | 7/1992 | Hilgers et al. ........................ 433/20 |
| 5,137,446 | 8/1992 | Yamauchi et al. ................... 433/20 |
| 5,167,499 | 12/1992 | Arndt et al. .......................... 433/7 |
| 5,167,500 | 12/1992 | Miura .................................. 433/7 |
| 5,288,230 | 2/1994 | Nikutowski et al. ................. 433/20 |

FOREIGN PATENT DOCUMENTS 56-89716 7/1981 Japan.

OTHER PUBLICATIONS

George F. Andreasen and Terry B. Hilleman, "An evaluation of 55 cobalt substituted Nitinol wire for use in orthodontics," *Journal of American Dental Association,* vol. 82, Jun. 1971, pp. 1373–1375.

M. F. Talass, DDS, MSC, "Optiflex Archwire Treatment of a Skeletal Class III Open Bite," *Journal of Clinical Orthodontics,* vol. 26, No. 4, pp. 245–246.

C. M. Wayman, "Some Applications of Shape-Memory Alloys," *Journal of Metals,* Jun., 1980, pp. 129–137.

John Wiley & Sons, "Shape-Memory Alloys," *Encyclopedia of Chemical Technology,* Third Ed., vol. 20, pp. 726–736.

*Primary Examiner*—Cary E. O'Connor
*Attorney, Agent, or Firm*—Frost & Jacobs

[57] ABSTRACT

An orthodontic wire for selectively moving teeth is provided. The wire comprises a first layer made from a first metallic material, and a second layer made from a second material, wherein the wire exhibits a predetermined degree of springback suitable for the selective movement of teeth. The first layer is preferably of a material which, because of its mechanical properties, would be suitable for use as an orthodontic wire by itself, and wherein the second layer is preferably of a material which has less elasticity than the material of the first layer, and this wire is capable of delivering a light, substantially continuous force to teeth when used in orthodontic treatment. The wire further has a cross-sectional area, and, when used in the orthodontic treatment of teeth, the wire can deliver a force which is lighter than that delivered by a wire of identical cross-sectional area made solely from the first layer. A method for selectively moving teeth is also provided, and utilizes the same wire.

21 Claims, 5 Drawing Sheets

ORTHODONTIC WIRE AND METHOD FOR THE MOVING OF TEETH

FIELD OF THE INVENTION

This invention relates to wires utilized for the orthodontic movement of teeth and also to a method for selectively moving teeth. More particularly, the wires of the present invention comprise a first layer of one material and a second layer made from another material, wherein at least one of the materials employed in the wire is a metallic substance which is of a type which would be suitable by itself as an orthodontic wire.

BACKGROUND OF THE INVENTION

The orthodontic treatment of misaligned teeth generally involves the attachment of brackets to the teeth, and the placement of a wire within these brackets to apply a controlled force to the teeth. The wires employed are typically formed, or "trained," into a desired shape such as an arch form, usually by heat treatment or cold forming. When a trained wire is placed within the brackets attached to the teeth, the practitioner deflects the wire, and, since the types of wire employed exhibit a significant amount of elasticity, it imparts a force against the bracket as it attempts to return to its "trained" shape. It will be apparent, therefore, that these wires should exhibit a relatively high degree of elasticity, or springback, so that the wires will not plasticly (i.e., permanently) deform when they are deflected. Obviously, if plastic deformation occurs, the wires will not attempt to return to their original shape, and thus no force will be applied to the teeth.

The ultimate goal of orthodontic treatment is the achievement of proper tooth alignment in the shortest period of time with the least amount of patient discomfort. Pain generally occurs when too great of a force is applied to the teeth, and excessive force can even lead to soft tissue damage and hard tissue destruction. In addition, it is also desirable to reduce the number of office visits as well as the duration of chair time during such visits. Orthodontic research has shown that optimal treatment is achieved by using a wire capable of delivering a relatively light but continuous force to the teeth. A light force is desirable for the reasons outlined previously, and a continuous force is desired so that frequent adjustments to the wire are not necessary. If the wire loses its ability to supply a moving force to the teeth too rapidly, the patient will have to return to the practitioner much more frequently for additional deflection of the wires. In addition, a wire that supplies a continuous force can usually provide more control to the practitioner. The ideal wire, therefore, is one that is capable of being deflected to a large degree without undergoing plastic (i.e., permanent) deformation, and thereafter supplies a continuous, light force to the teeth as the wire attempts to restore itself to its original shape. Other desirable characteristics for these wires include formability, i.e. the ability of the wire to be fabricated in a number of different shapes by the practitioner, the capability of being manufactured in different colors (for aesthetic purposes), resistance to the corrosive fluids found in the human mouth, and a smooth surface for reduced friction.

Numerous types of wires have been employed in orthodontic treatment, and each has its own unique characteristics. In general, however, the force applied by any wire to the teeth is determined, in part, by the size of the wire, with smaller diameter wires imparting a lighter force. Thus, at least initially, the practitioner will utilize a wire of relatively small cross-section. These smaller wires, however, offer less control to the practitioner since they will not fill the bracket slots.

The brackets utilized, whether they are banded or bonded to the teeth, have either a slot or tube into which the wire is inserted, and these slots or tubes are significantly larger than the size of the small wires initially used during treatment. Thus, there is a considerable amount of play between the wire and the brackets, which in turn reduces the amount of directional control the practitioner has, since the wires will tend to shift, float and/or rotate within the brackets. When larger diameter wires, and in particular those of rectangular cross-section, are employed, the orthodontist is able to take advantage of the tips, torques and axial angulation built into the bracket slots which can provide precise directional movements to the teeth. Ideally one would like to use a wire of rectangular cross-section that is only slightly smaller than the size of the brackets. These wires will substantially fill the bracket slots, thereby enabling the practitioner to make full use of the entire slot or tube in the bracket. Unfortunately, however, there are no currently-available orthodontic wires which deliver the desired light force and yet are of a cross-section which fills the slot or tubes of the brackets.

While a simple solution might appear to be merely reducing the size of the bracket slots or tubes, this is not practical. The practitioner may often need to impart greater forces to the teeth in the later stages of the treatment process to complete the tooth alignment process. It is impractical and expensive, however, for the practitioner to change the brackets throughout the treatment process in order to accommodate different diameter wires. In addition, and more significantly, a further reduction in the slot or tube size from that commonly employed is not practical because manufacturing tolerances are such that the sizes which would be needed so that the "light-force" wires would fill the slot or tube cannot be uniformly produced with currently available manufacturing equipment, and these smaller slots and tubes would not be capable of withstanding the forces applied by the wires.

Various types of wires have been employed in orthodontic treatment, and these include: stainless steel, chrome-cobalt alloys, Elgiloy (chrome-cobalt-nickel alloys), nickel-cobalt alloys, gold alloys (65% Au-5% Pt-2% Pd-15% Cu-10% Ag), nitinol (55% Ni-45% Ti), beta-titanium (79% Ti-11% Mo-6% Zr-4% Sn) and numerous other compositions. Each of these wires has its own unique characteristics, and cost is certainly one significant variant. In the past, stainless steel was often the alloy of choice, as it is not only corrosive-resistant, but could be deflected to some degree without undergoing plastic deformation. Stainless steel is relatively stiff as compared to other wires used in orthodontics, since more force is required to deflect stainless steel wires. Because of this stiffness, however, the unloading force in stainless steel after such a deflection, i.e., the force applied to the teeth, is much greater for a given deflection. Unfortunately, however, the elasticity (or springback) of stainless steel is not as great as one would desire, and therefore these wires rapidly loose their effectiveness. In other words, while stainless steel wires can deliver a large force through a small deflection, this force rapidly diminishes as the teeth begin to move. This in turn results in relatively short intervals between visits to the orthodontist since the wires must be deflected again so that a restorative force will be delivered to the teeth. In addition, patient discomfort is also increased due to the stiffness of these wires.

Nitinol, or nickel-titanium memory metal as it is sometimes referred to, has been widely used since its potential in orthodontics was first noted in the early 1970's (U.S. Pat. No. 4,037,324). These wires generally are capable of being deflected to a greater degree than stainless steel without undergoing plastic deformation, and the restorative force applied to the teeth after such a deflection is more constant than that delivered by stainless steel. In addition, even the initial forces applied by these wires is much less than a stainless steel wire of identical diameter. As one skilled in the art is aware, an ideal wire is one that applies a light and continuous corrective force to the teeth. The light force results in less patient discomfort and decreased risk of tissue damage, and the ability to maintain a constant force over a longer length of time means that the intervals between visits to the orthodontist can be increased. The most significant problem with Ni-Ti wires is that a full-size wire, i.e. one having a sufficient diameter to fill the bracket slots, imparts too large of a force to the teeth during the initial stages of treatment. Thus, smaller diameter Ni-Ti wires are typically used during the initial stages of treatment, thereby resulting in a reduction in directional control.

Consequently, heretofore there has not been available a single-stranded orthodontic wire capable of delivering light, continuous correctional forces to teeth while at the same time being of a sufficiently large diameter to enable the practitioner to completely fill the bracket slot or tube and thereby take full advantage of the bracket slots or tubes.

SUMMARY OF THE INVENTION

While not exclusive, the following describes some of the important features and objectives of the present invention.

It is an object of the present invention to provide an improved orthodontic wire which is capable of imparting a light, continuous corrective force to the teeth.

It is yet another object of the present invention to provide an orthodontic wire which is capable of imparting a light, continuous corrective force to the teeth wherein the wire is of sufficiently large diameter to substantially fill the slots or tubes of the brackets attached to the teeth.

It is still another object of the present invention to provide an improved method for selectively moving teeth wherein said movement is caused by a wire capable of delivering a light and continuous force to the teeth.

It is another object of the present invention to provide an orthodontic wire having a layered construction, wherein the properties of the wire can be adjusted by varying the materials or relative amounts of each layer, while still providing a wire capable of imparting a light corrective force to teeth and substantially filling standard orthodontic brackets.

It is still another object of the present invention to provide a force imparting orthodontic device capable of delivering a continuous corrective force to teeth.

The foregoing objects can be accomplished, in accordance with one aspect of the invention, by providing an orthodontic wire for selectively moving teeth, said wire comprising a first layer made from a first metallic material, and a second layer made from a second material, wherein the wire exhibits a predetermined degree of springback suitable for the selective movement of teeth. The first layer is preferably of a material which, because of its mechanical properties, would be suitable for use as an orthodontic wire by itself, and wherein the second layer is preferably of a material which has less elasticity than the material of the first layer, and this wire is capable of delivering a light, substantially continuous force to teeth when used in orthodontic treatment. The wire further has a cross-sectional area, and, when used in the orthodontic treatment of teeth, said wire can deliver a force which is lighter than that delivered by a wire of identical cross-sectional area made solely from said first layer. The first and second layers are preferably cladded or braided to one another, however other manufacturing methods may be employed. The first layer may comprise a core, with the said second layer comprising a sheath disposed about said core. The first metallic material can be chosen from the group consisting of: stainless steel, nitinol alloys, Elgiloy (chrome-cobalt-nickel alloys), nickel-cobalt alloys, gold alloys, and beta-titanium alloys. The second material can be chosen from the group consisting of: titanium, titanium alloys, niobium, niobium alloys, and numerous of other alloys exhibiting the requisite low elasticity. The preferred combination is wherein the first layer is nitinol alloy, and the second layer is niobium-titanium. The wire may also be straight or as a pre-formed shape such as an arch, or used in the construction of an orthodontic or dental force imparting device chosen from the group consisting of: coil springs, separator springs, quad helixes, lingual arches, retainers, palatial expanders, preformed springs, uprighting springs, retraction springs, intraoral elastics. In other words, the wire of the present invention may be used in any dental or orthodontic device which would benefit from its unique properties.

A method for selectively moving teeth is also provided, and comprises the steps of: (a) attaching a plurality of brackets to a plurality of teeth; (b) positioning an orthodontic wire within said plurality of brackets, said wire having a preformed shape, wherein said wire is deflected from its original shape by application of a loading force; and (c) permitting said deformed wire to return towards its original shape, thereby causing said plurality of teeth to move with said return of said wire; wherein said wire comprises a first metallic layer and a second layer, said first and second layers are of two distinct materials, and said wire exhibits a predetermined degree of springback suitable for the selective movement of teeth. All of the features for the wire described above can thus be employed in this method.

BRIEF DESCRIPTION OF THE DRAWINGS

While the specification concludes with claims particularly pointing out and distinctly claiming the present invention, it is believed that the same will be better understood from the following description taken in conjunction with the accompanying drawings in which:

DETAILED DESCRIPTION OF THE INVENTION

Figure 1:
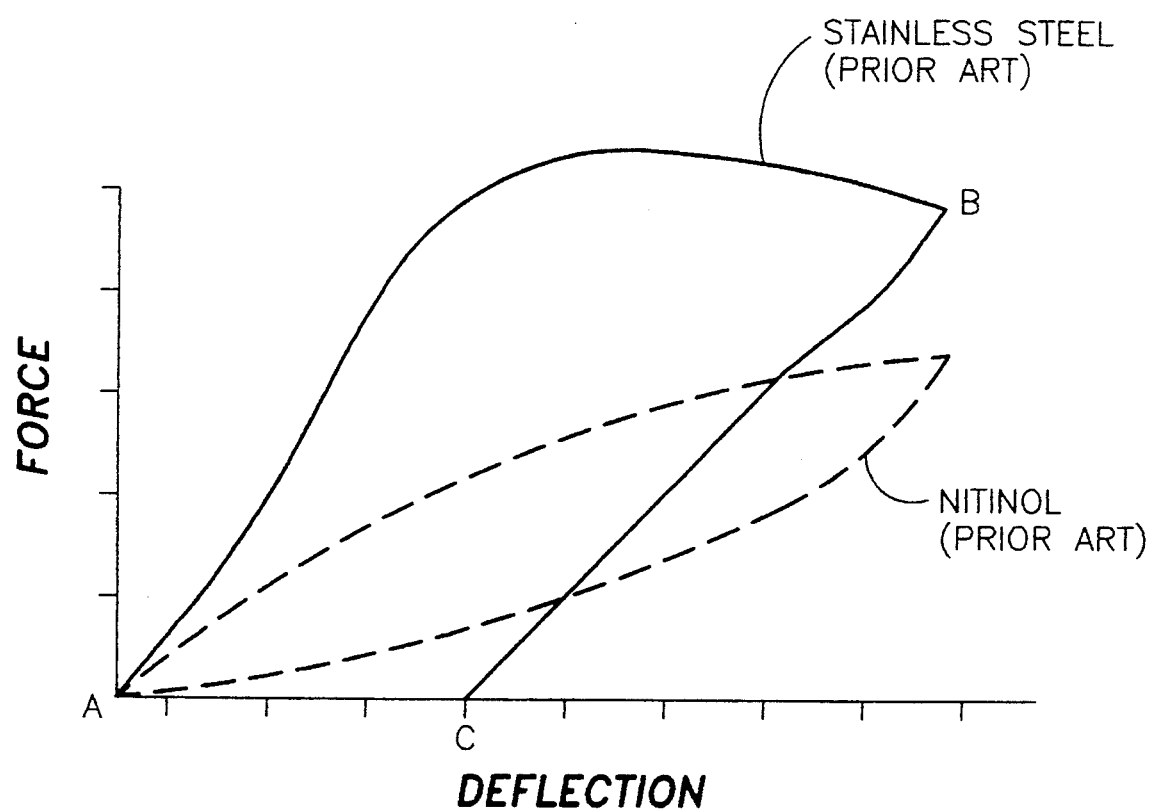
FIG. 1 is a plot of force v. deflection for typical prior art orthodontic wires.

Referring now to the drawings in detail, FIG. 1 graphically depicts the forces imparted by two types of prior art orthodontic wires, namely stainless steel and nitinol, during and after deflection. The plot for each wire has a loading and unloading portion, the loading phase generally indicating the amount of force which must be applied to the wire in order to deflect it a given amount and the unloading phase indicating the amount of force applied by the wire as it attempts to return to its original shape. For a typical stainless steel wire for example, the loading phase is the portion of the plot between points A and B, and the unloading phase is between points B and C.

As shown in FIG. 1, a stainless steel orthodontic wire will begin to plasticly deform at some point during loading, since the force needed to deflect the wire begins to decrease at this point. In other words, the wire begins to take a set when the amount of deflection exceeds this limit, and thus the wire will not completely return to its original shape during the unloading phase. These wires, therefore, can only be deformed a small amount by the practitioner (as compared to a typical nitinol wire) before plastic deformation occurs. The point at which a wire begins to plasticly deform is often quantified in terms of yield strength, and thus a wire having a greater yield strength can be deflected a greater amount before plastic deformation will occur.

As compared to a comparably-sized nitinol wire, it is also apparent that stainless steel wire requires much more force to produce a given deflection (i.e., is stiffer), and therefore provides a much greater force to the teeth during the unloading phase. This stiffness can be quantified in terms of the elastic modulus of the wire, such that stainless steel wire has a greater elastic modulus when compared to a nitinol wire of similar cross-section. Although stainless steel wire is stiffer, the force imparted by the wire as it attempts to return to its original shape decays rapidly as the deflection decreases, and reaches zero well before the wire has completely returned to its original shape. Thus, stainless steel wires necessitate more frequent attention by the practitioner, as the wires must be redeflected once they are no longer applying directional movement force to the teeth. In addition, since stainless steel wires are rather stiff (as demonstrated by the amount of force required for deflection) relatively small diameter wires must be employed in order to deliver the desired light corrective forces to the teeth. These small diameter wires will not properly fill the slots or tubes of the brackets, thereby resulting in a loss of control.

In terms of quantifiable properties, orthodontic wires should have a relatively low elastic modulus (i.e., less stiff), and a relatively high yield strength (can be deflected without plasticly deforming or fracturing). Such wires will deliver the lighter, more continuous force that is desired. The ratio of yield strength to elastic modulus is often referred to as the "springback" of the wire, and it should be apparent, therefore, that the greater the amount of springback, the more ideal the wire for orthodontic purposes. While stainless steel wires can be effectively employed for orthodontic purposes, they are certainly far from ideal. This is particularly true when one considers that a stainless steel wire of relatively small diameter will have to be employed during the early stages of treatment, thereby resulting in a loss of control.

As also shown in FIG. 1, nitinol wires exhibit properties much more conducive to efficient orthodontic treatment due to their increased springback or elasticity. A lighter force is required to deflect the wires than stainless steel (lower elastic modulus), and in turn a lower corrective force is applied to the teeth during the unloading phase. Nitinol wires also do not exhibit any plastic deformation over the range of deflections commonly utilized for orthodontic treatment, as the force required for deflection does not decrease. Most importantly, these wires apply a more constant force during the unloading phase, as the force does not decay as rapidly as stainless steel.

It should be kept in mind that wire diameter also affects the amount of corrective force applied to the teeth, and the wires depicted in FIG. 1 are of comparable diameter. For example, a rectangular $0.0215 \times 0.0255$ inch nitinol wire will supply a greater corrective force than a round 0.014 inch nitinol wire, however the shape of wires force-deflection plots will be nearly identical. Most common bracket widths currently used are $0.018 \times 0.028$ inches and $0.022 \times 0.028$ inches, and a wire having a slightly smaller width than the bracket yet still capable of delivering continuous, light corrective forces to the teeth is most desirable. While the $0.0215 \times 0.0255$ wire will fill a $0.022 \times 0.028$ bracket, and therefore enable the practitioner to take full advantage of the slot or tube of the bracket, the force delivered by such a wire would generally be too large for use during the initial stages of treatment. The practitioner will therefore have to begin the treatment process with, for example, a 0.014 wire, thus delivering a light force to the teeth but losing a considerable amount of directional control. Ideally, an orthodontic wire for the initial stages of treatment should deliver a constant light force even after considerable deflection, and of course it is desired that such a wire fill even the largest bracket slot which a practitioner might employ.

Figure 2:
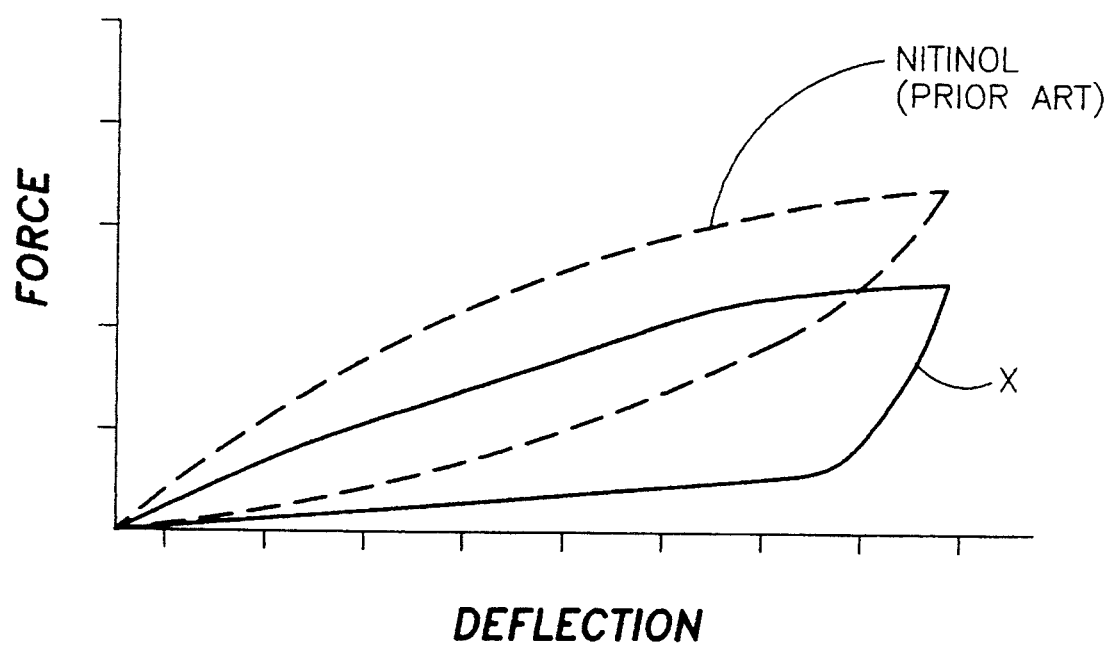
FIG. 2 is an exemplary plot of force v. deflection for the orthodontic wire of the present invention, along with the same plot for a prior art nitinol wire.

FIG. 2 is a plot similar to that of FIG. 1, however it depicts an exemplary orthodontic wire according to the present invention (labeled as wire X) along with an exemplary nitinol orthodontic wire. Both wires depicted in FIG. 2 are of an identical diameter, and, for example, may be of a $0.0215 \times 0.0255$ rectangular configuration. As shown in FIG. 2, the wire according to the present invention will exhibit an unloading portion which is similar to that of a nitinol wire of much smaller diameter, and in fact is flatter. In other words, the wire of the present invention will deliver a lighter, more continuous force to the teeth than a comparably-sized nitinol wire. The practitioner will be able to place a wire of the present invention having a diameter which will substantially fill a the slot or tube of a conventional bracket, thereby optimizing the control of tooth movement by utilizing the angulation and torquing surfaces of the brackets, while maintaining the desired light corrective forces. Heretofore it has not been possible to achieve both a filling of the slot or tube, and a light corrective force with the same wire. With the wire of the present invention the practitioner will be able to make full use of the angulation and torquing surfaces, as well as the "ins and outs," of the brackets even during the initial stages of orthodontic treatment.

The wires of the present invention generally comprise a first layer of one material and a second layer which is made from another material, with at least one of these materials being a metallic substance which exhibits a degree of springback (or elasticity) suitable for orthodontic wire. In other words, at least one of the materials would be suitable for use as an orthodontic wire by itself, since it exhibits the desired degree of springback. The resulting wire, however, will impart less force to the teeth as compared to a wire of identical cross-section made solely from the material suitable for orthodontic use. By proper selection of the materials employed, an orthodontic wire providing light and continuous corrective forces, yet having the necessary size to completely fill the slots or tubes of the brackets, can be obtained. The metallic material used for the first layer will preferably exhibit properties similar to that which is ultimately desired in terms of the level of force imparted to the teeth and the constancy of this force. The second material will preferably be a "neutral" layer, meaning that it does not adversely affect either the strength or constancy of the force applied to the teeth by the first metallic material. A neutral layer will generally be much less elastic than the first metallic material, and it has been found such a layer will produce the desired results. Thus, the orthodontic wire of the present invention, even though it comprises first and second distinct materials in separate layers, will exhibit unloading properties nearly equivalent to the first, or active layer, metallic material. Obviously by providing a second neutral layer, the diameter of the wire is increased, and in fact, the diameter can be increased so that the wire will substantially fill the slot or tube of the bracket. Of course it is also possible to utilize a non-neutral material for the second layer, wherein this material will contribute to the strength, memory, and elasticity of the final product.

Figure 3:
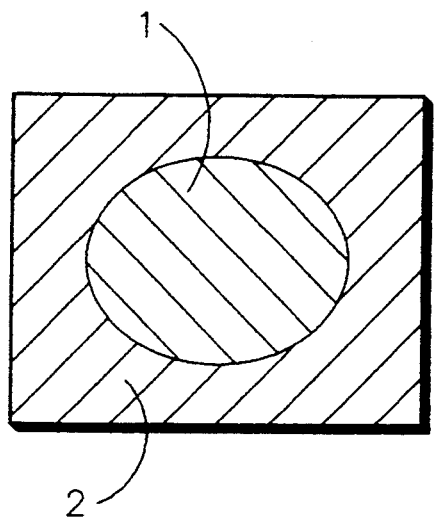
FIG. 3 is a cross-sectional view of an orthodontic wire according to the present invention.

A preferred embodiment of the wire according to the present invention is shown in FIG. 3, wherein one layer comprises a core of oval cross-section and the second layer comprises a rectangular shell. The first, or active metallic layer may comprise either the core or the shell, however it is preferred that the active layer comprise the core. The active layer can be made of any of the previously known materials used for orthodontic wires, including stainless steel, nitinol, gold alloy and beta-titanium. If, in fact, the active layer is the core material, it may even be possible to use non-traditional materials which by themselves may be problematic as materials for orthodontic wires. For example, if the active material is such that it would normally corrode in the oral environment, a neutral sheath will protect the core material and thus provide even greater flexibility in the choice of materials. In addition, some people are allergic to materials such as nickel, and an appropriate sheath may prevent an adverse reaction. It is also desirable that one have the ability to color the wire for cosmetic reasons, such as by anodization, and thus it is preferred that the shell be anodizable. Examples of anodizable materials suitable for the shell include various titanium alloys such as Nb/Ti, titanium itself, and Ti[6-4].

The wire of the present invention whose properties would be as depicted by FIG. 2 has a cross-sectional structure as shown in FIG. 3. The core 1 comprises titanium, although various other "neutral" materials could also be employed for the core. The sheath 2 in the embodiment of FIGS. 2 and 3 is a nitinol alloy of 55% nickel and 45% titanium. As discussed above, this active sheath could be made of any of a number of materials, and nitinol is merely a presently preferred material. Since the neutral titanium layer exhibits relatively little springback or elasticity, the unloading properties of the wire are relatively unchanged from that of the sheath material. While the resulting wire, as shown in FIG. 2, is somewhat stiffer than a non-layered nitinol wire having a cross-section similar to that of active layer of FIG. 2, this is mush less significant, at least for orthodontic treatment purposes, than the unloading properties present in the wire.

Figure 4:
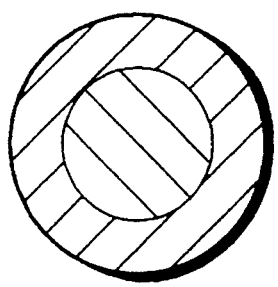
FIG. 4 is a cross-sectional view of another orthodontic wire according to the present invention.
Figure 5:
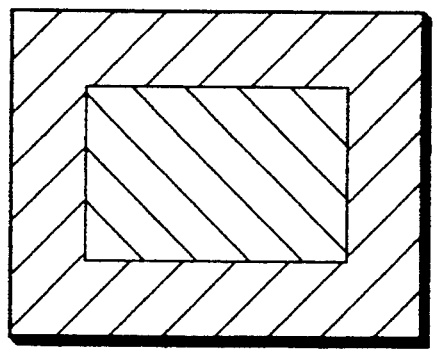
FIG. 5 is a cross-sectional view of yet another orthodontic wire according to the present invention.
Figure 6:
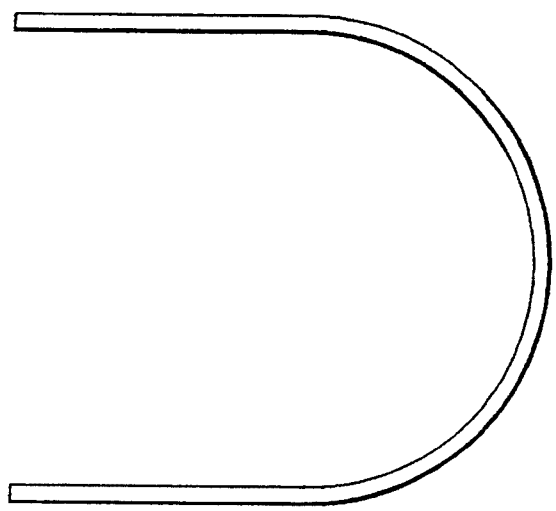
FIG. 6 is a top plan view of an archwire made according to the present invention.
Figure 7:
FIG. 7 is a plan view of a coil spring made according to the present invention.
Figure 8:
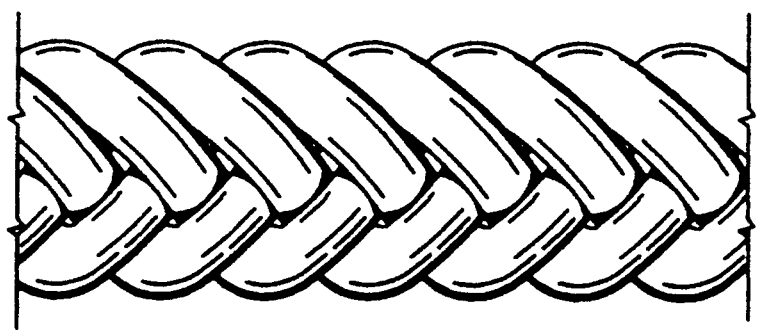

It should also be noted that the wires of the present invention are not limited to rectangular cross-section, as nearly any shape can be manufactured. For example, the core material can be round with the outer sheath of rectangular cross-section, or vice-versa. FIGS. 4 and 5 depict two alternative configurations that may be employed. In addition, the wires can be made into any pre-formed device commonly employed in the orthodontic field. These devices would all benefit from the use of a wire capable of delivering a constant light force while being of a larger diameter, and the following devices could thus be made using the wire of the present invention: As shown in FIG. 6, for example, a common appliance which could be manufactured is a pre-formed dental arch. Depending on the method of treatment, these pre-formed arches may often be the wire of choice, as opposed to straight wires which the practitioner must form into the desired shape. The archwire of FIG. 6 may also be subjected to varying degrees of heat treatment, as known in the art, in order to improve its ease of use by the practitioner. The wires of the present invention can also be utilized to produce coil springs, as shown by FIG. 7, as well as other force imparting orthodontic devices which are commonly used by practitioners to selectively move teeth, including: coil springs, separator springs, quad helixes, lingual arches, retainers, palatial expanders, preformed springs, uprighting springs, retraction springs, intraoral elastics.

One of the most significant advantages of the wires of the present invention is that a series of wires capable of imparting different levels of force to the teeth yet having the same cross-sectional diameter can be produced. Thus, each wire which the practitioner employs will fill the slot or tube of the bracket completely, enabling one to take advantage of the entire slot or tube while still having a choice of force levels. This latter aspect has heretofore not been possible with any previously available orthodontic wires. The ultimate result is that the duration of treatment will be reduced, and the length of office visits also decreased since the practitioner will have much more control over the treatment process. Likewise, if desired, wires imparting equivalent forces to teeth yet having different diameters may also be produced.

The wires of the present invention can be produced by any of a number of methods, however the presently preferred one involves inserting the core material into a can of slightly larger diameter, filling the space between the core and the can with a powdered form of the sheath material, and subjecting this structure to a known hot isostatic pressure process (HIP). This process utilizes heat and pressure to clad the two materials to one another, and is much less expensive than an extrusion process. Of course extrusion, cladding, and various other methods could be employed to produce the wires of the present invention. The preferred process tends to flatten the core material to some extent, thereby forming a somewhat oval core. The desired properties, however, are maintained.

It is also possible to form the wires of the present invention by other means. For example, the wires can be made such that both the core and sheath are round, rectangular or square, and these embodiments are well within the scope of the present invention. In addition, the desired results can be achieved by a wire wherein the first and second layers are circular, rectangular or square wires of the preferred materials that have been cladded to one another such as shown by FIGS. 4 and 5. Numerous other configurations could also be produced, as long as the wire has first and second layers of the specified properties.

Braided wires have also become quite common in the orthodontic industry, and the wires of the present invention can be utilized in such structure. In fact, it is within the scope of the present invention to provide a braided wire made of two or more distinct materials. In other words, the advantageous properties achieved by a wire of the core and sheath design can also be accomplished by providing a braided wire wherein one or more wires of the first (active) layer are braided to one or more wires made from the second (preferably neutral) layer. The term braiding is intended to signify the intertwining of two or more layers. By active it is meant that the layer would be suitable for use as an orthodontic wire by itself, while a neutral layer means that the material exhibits less springback than the active layer. Such a configuration results in a braided wire which provides the light, continuous force, yet is of a sufficient cross-sectional diameter to substantially fill the brackets. Of course the number of strands of each material used to manufacture the braided wire can be varied in order to achieve braided wires having various force-imparting properties.

It will be understood that modifications may be made in the invention without departing from the spirit of it. For example, a wire made from three or more layers would be well within the scope of the present invention. Accordingly, the scope of the present invention should be considered in terms of the following claims, and it is understood not to be limited to that shown and described in the specification.

What I claim is:

1. A method for selectively moving teeth comprising the steps of:
   (a) attaching a plurality of brackets to a plurality of teeth;
   (b) positioning an orthodontic wire within said plurality of brackets, said wire having a preformed shape, wherein said wire is deflected from its original shape by application of a loading force; and
   (c) permitting said deformed wire to return towards its original shape, thereby causing said plurality of teeth to move with said return of said wire;
   wherein said wire comprises a first metallic layer and a metallic second layer, said first and second layers are of two distinct materials, and said wire exhibits a predetermined degree of springback suitable for the selective movement of teeth.

2. The method of claim 1, wherein said first layer is of a material which, because of its mechanical properties, would be suitable for use as an orthodontic wire by itself, and wherein said second layer is of a material which has less elasticity than the material of the first layer, and wherein said wire delivers a light, substantially continuous force to said teeth.

3. The method of claim 2, wherein one of said first and second layers comprises a core, and the other of said first and second layers comprises a substantially continuous sheath disposed about said core.

4. The method of claim 3, wherein said core and said sheath are cladded to one another.

5. The method of claim 4, wherein said second layer is of a material chosen from the group consisting of: titanium, titanium alloys, niobium, niobium alloys.

6. The method of claim 2, wherein said first and second layers are braided to one another.

7. The method of claim 2, wherein said first metallic layer is of a material chosen from the group consisting of: stainless steel, nitinol alloys, chrome-cobalt-nickel alloys, nickel-cobalt alloys, gold alloys, and beta-titanium alloys.

8. An orthodontic wire for selectively moving teeth, said wire comprising a first layer made from a first metallic material, and a second layer made from a second metallic material, and said wire exhibits a predetermined degree of springback suitable for the selective movement of teeth.

9. The wire of claim 8, wherein said first layer is of a material which, because of its mechanical properties, would be suitable for use as an orthodontic wire by itself, and wherein said second layer is of a material which has less elasticity than the material of the first layer, and wherein said wire is capable of delivering a light, substantially continuous force to teeth when used in orthodontic treatment.

10. The wire of claim 9, wherein said wire has a cross-sectional area, and, when used in the orthodontic treatment of teeth, said wire can deliver a force which is lighter than that delivered by a wire of identical cross-sectional area made solely from said first layer.

11. The orthodontic wire of claim 10, wherein said first and second layers are cladded to one another.

12. The orthodontic wire of claim 11, wherein said first layer comprises a core, and said second layer comprises a sheath disposed about said core.

13. The orthodontic wire of claim 10, wherein said first and second layers are braided to one another.

14. The orthodontic wire of claim 10, wherein said first metallic material is chosen from the group consisting of: stainless steel, nitinol alloys, chrome-cobalt-nickel alloys, nickel-cobalt alloys, gold alloys, and beta-titanium alloys 15. The orthodontic wire of claim 14, wherein said second material is chosen from the group consisting of: titanium, titanium alloys, niobium, and niobium alloys.

16. The orthodontic wire of claim 14, wherein said first layer is nitinol alloy, and said second layer is niobium-titanium.

17. The orthodontic wire of claim 10, wherein said wire is in the shape of a pre-formed arch.

18. The orthodontic wire of claim 10, wherein said wire is in the shape suitable for use in a force imparting orthodontic or dental device chosen from the group consisting of: coil springs, separator springs, quad helixes, lingual arches, retainers, palatial expanders, preformed springs, uprighting springs, retraction springs, and intraoral elastics.

19. An orthodontic wire for selectively moving teeth, said wire comprising a first layer made from a first metallic material, and a second layer made from a second metallic material, wherein said first material is of a type suitable for use as an orthodontic wire alone, wherein said wire exhibits a predetermined degree of elasticity suitable for the selective movement of teeth, and wherein said wire imparts a substantially continuous force to teeth when used in orthodontic treatment, wherein said force is less than that produced by an orthodontic wire of identical cross-section manufactured solely from said first material.

20. The orthodontic wire of claim 19, wherein said first layer is nitinol alloy, and said second layer is niobium-titanium.

21. A method for selectively moving teeth comprising the steps of:

(a) attaching a plurality of brackets to a plurality of teeth;

(b) positioning an orthodontic wire within said plurality of brackets, said wire having a preformed shape, wherein said wire is deflected from its original shape by application of a loading force; and (c) permitting said deformed wire to return towards its original shape, thereby causing said plurality of teeth to move with said return of said wire;

wherein said wire comprises a first metallic layer and a second layer, said first and second layers are of two distinct materials, said wire exhibits a predetermined degree of springback suitable for the selective movement of teeth, said first layer is of a material which, because of its mechanical properties, would be suitable for use as an orthodontic wire by itself, said second layer is of a material which has less elasticity than the material of the first layer, wherein said wire delivers a light, substantially continuous force to said teeth, and said first and second layers are braided to one another.

* * * * *